US00PP35569P3

(12) United States Plant Patent
Castellarin et al.

(10) Patent No.: US PP35,569 P3
(45) Date of Patent: Jan. 9, 2024

(54) GRAPEVINE PLANT NAMED 'TRASEMIS'

(50) Latin Name: ***Vitis vinifera* L.**
Varietal Denomination: TRASEMIS

(71) Applicants: UNIVERSITÀ DEGLI STUDI DI UDINE, Udine (IT); ISTITUTO DI GENOMICA APPLICATA, Udine (IT)

(72) Inventors: Simone Diego Castellarin, Vancouver (CA); Guido Cipriani, Faedis (IT); Gabriele Di Gaspero, Cividale del Friuli (IT); Michele Morgante, Tricesimo (IT); Enrico Peterlunger, Codroipo (IT); Raffaele Testolin, Udine (IT)

(73) Assignees: Università degli Studi di Udine, Udine (IT); Istituto di Genomica Applicata, Udine (IT)

( * ) Notice: Subject to any disclaimer, the term of this patent is extended or adjusted under 35 U.S.C. 154(b) by 0 days.

(21) Appl. No.: 18/084,153

(22) Filed: Dec. 19, 2022

(65) Prior Publication Data

US 2023/0200271 P1 Jun. 22, 2023

(30) Foreign Application Priority Data

Dec. 21, 2021 (QZ) ..... PBR 20213392

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812
See application file for complete search history.

*Primary Examiner* — Kent L Bell
(74) *Attorney, Agent, or Firm* — Klarquist Sparkman, LLP

(57) ABSTRACT

A new grapevine variety distinguished by its leaf blistering, length of teeth, blade size, bunch length, area of anthocyanin coloration of main veins on upper side of blade of mature leaf, goffering of blade of mature leaf, resistance to downy and powdery mildew and winterhardiness.

4 Drawing Sheets

Genus and species: *Vitis vinifera* L.
Variety denomination: 'TRASEMIS'.

CROSS REFERENCE TO RELATED APPLICATIONS

This application claims the benefit of priority from QZ Community Plant Variety Office (CPVO) Application No. 20213392, filed Dec. 21, 2021.

BACKGROUND

The present application relates to a new and distinct variety of grapevine named 'TRASEMIS'. Our new plant resulted from a planned hybridization program and is a selection from crossing 'SK-00-1/10' (unpatented) as the seed parent with 'TRAMINER'(unpatented) as the pollen parent in 2009. The resulting plant was selected in 2017 when growing in a cultivated area in Udine, Italy.

SUMMARY

The 'TRASEMIS' variety is distinguished from other grapevine varieties due to the following unique combination of characteristics: leaf blistering, length of teeth, blade size, bunch length, area of anthocyanin coloration of main veins on upper side of blade of mature leaf, goffering of blade of mature leaf, resistance to downy and powdery mildew and winterhardiness. 'TRASEMIS' is distinguished from the male parent 'TRAMINER' as described in Table 1.

TABLE 1

Comparison to male parent.

| Characteristic | 'TRASEMIS' | Male Parent 'TRAMINER' |
|---|---|---|
| Leaf Blistering | Absent or Very Weak | Strong |
| Length of Teeth | Medium | Very Small |
| Size of Blade | Medium | Small |
| Mature Leaf: area of anthocyanin coloration of main veins on upper side of blade | Up to the 2nd bifurcation | Absent |
| Mature Leaf: goffering of blade | Weak | Very strong |
| Bunch Length (peduncle excluded) | Medium | Short |
| Disease Resistance | Resistant to downy mildew and to powdery mildew | No resistance to downy mildew or to powdery mildew |
| Winter Hardiness | Resists up to −23° C. | Resists up to −18° C. |

'TRASEMIS' is distinguished from the female parent 'SK-00-1/10' as described in Table 2.

TABLE 2

Comparison to female parent.

| Characteristic | 'TRASEMIS' | Female Parent 'SK-00-1/10' |
|---|---|---|
| Flower: sexual organs | Fully developed stamens and fully developed gynoecium | Reflexed stamens and fully developed gynoecium |

TABLE 2-continued

| Comparison to female parent. | | |
|---|---|---|
| Characteristic | 'TRASEMIS' | Female Parent 'SK-00-1/10' |
| Berry: color of skin | Yellow rose | Yellow |
| Mature Leaf: size of blade | Medium | Large |
| Mature Leaf: shape of blade | Circular | Wedge-shaped |

Of the many commercial cultivars known to the present inventors, the most similar to the new grapevine 'TRASEMIS' is 'TRAMINER', to which a comparison has been provided above.

Asexual reproduction of this new variety by vegetative cuttings shows that the foregoing characteristics come true to form, are firmly fixed, and are established and transmitted through succeeding propagations, thus the new cultivar reproduces true to type. The cuttings are grafted onto K5BB rootstock clone VCR 102. The new variety was asexually reproduced in Rauscedo (PN), Italy.

Certain characteristics of this variety may change with changing environmental conditions (such as photoperiod, temperature, moisture, soil conditions, nutrient availability, or other factors). Color descriptions and other terminology are used in accordance with their ordinary dictionary descriptions unless the context clearly indicates otherwise. Color designations (hue/value/chroma) are made with reference to The Royal Horticultural Society (R.H.S.) Colour Chart, 6$^{th}$ edition, London, England, 2019.

Figure 1:
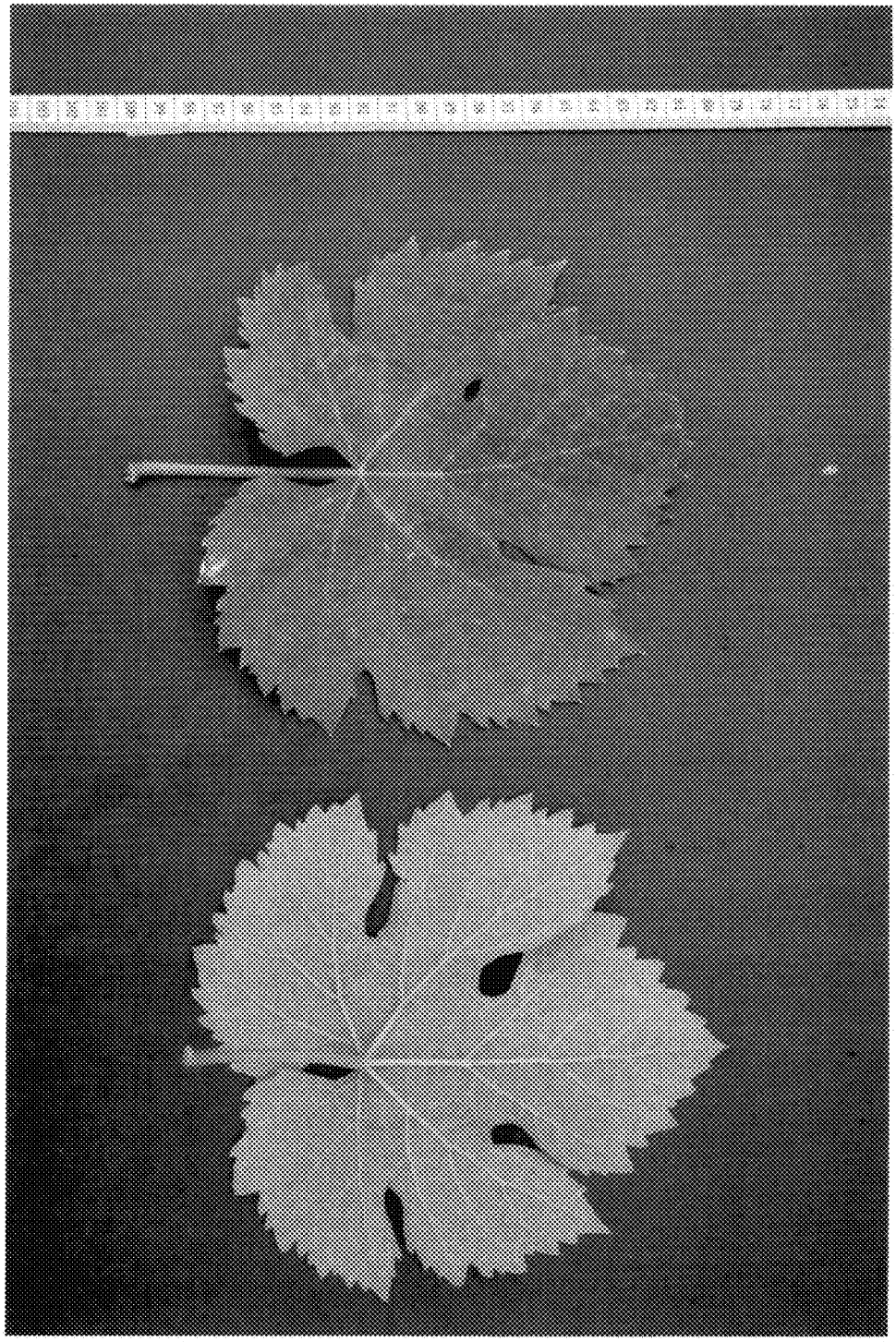
FIG. 1 is a photograph showing a mature leaf from a four year old plant of the new variety 'TRASEMIS' taken on Jun. 10, 2021, in Rauscedo (PN), Italy.
Figure 2:
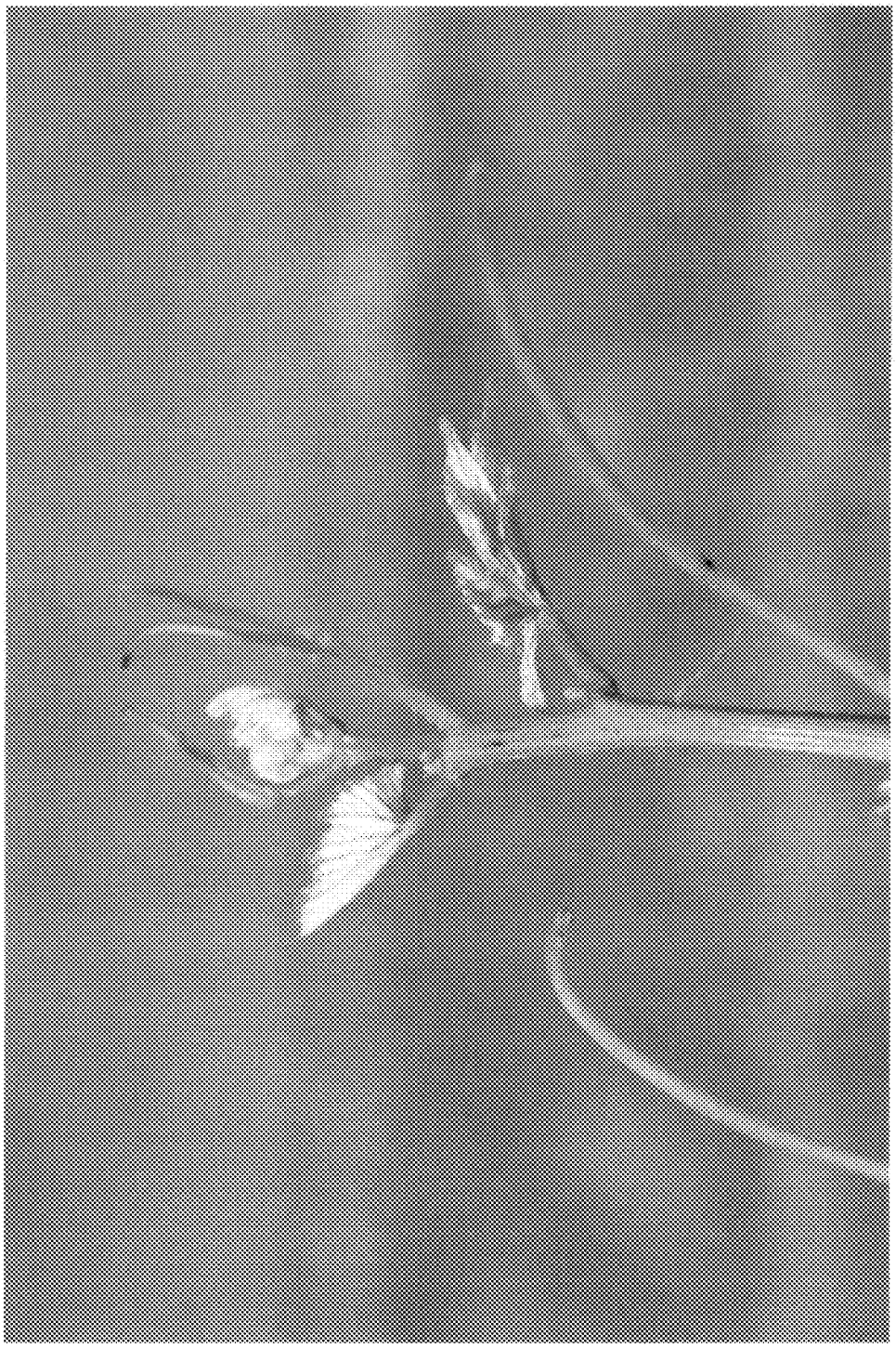
FIG. 2 is a photograph showing a shoot tip from a four year old plant of the new variety 'TRASEMIS' taken on May 21, 2021, in Rauscedo (PN), Italy.
Figure 3:
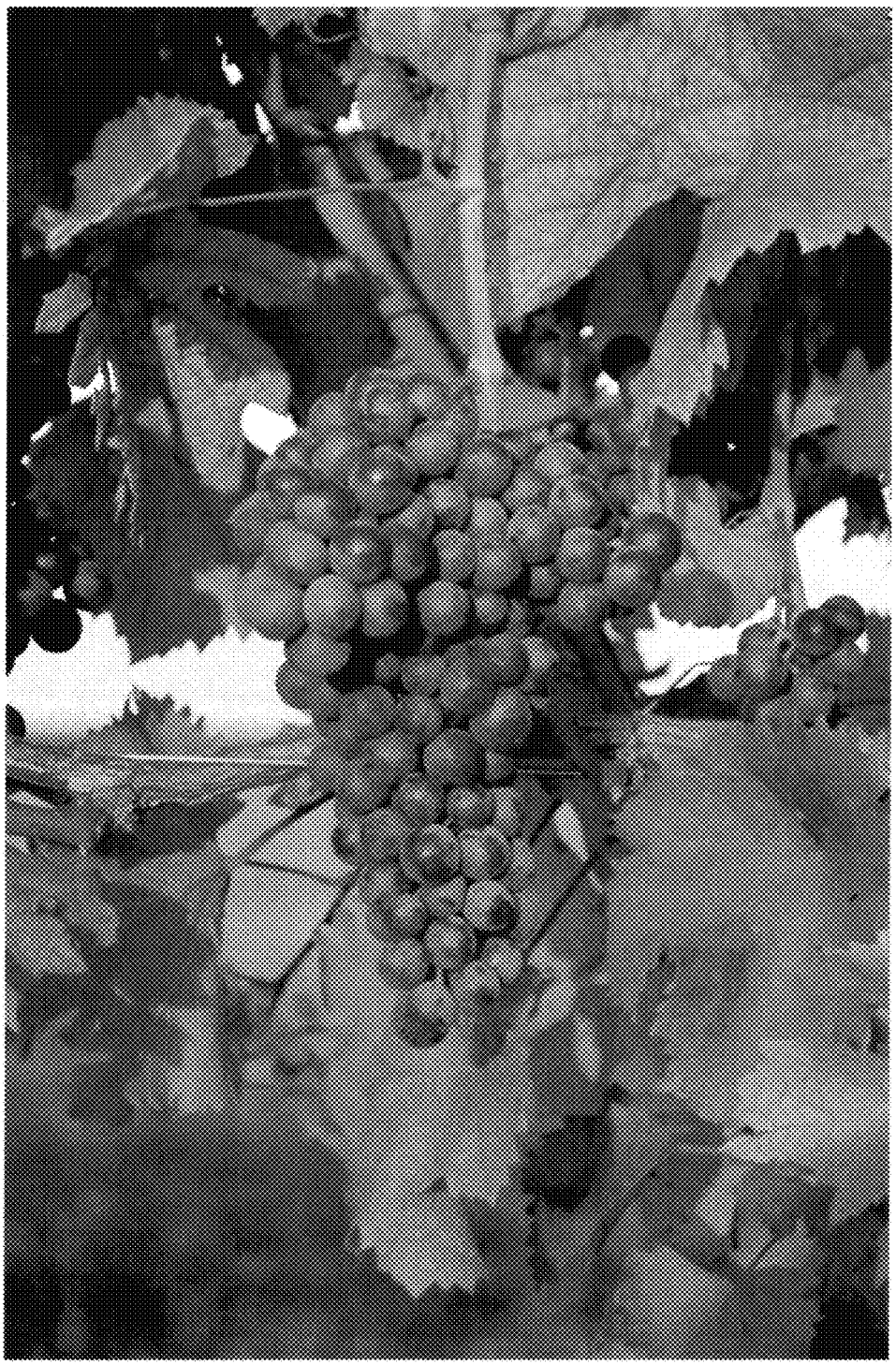
FIG. 3 is a photograph showing fruit from a four year old plant of the new variety 'TRASEMIS' taken on Sep. 14, 2021, in Rauscedo (PN), Italy.
Figure 4:
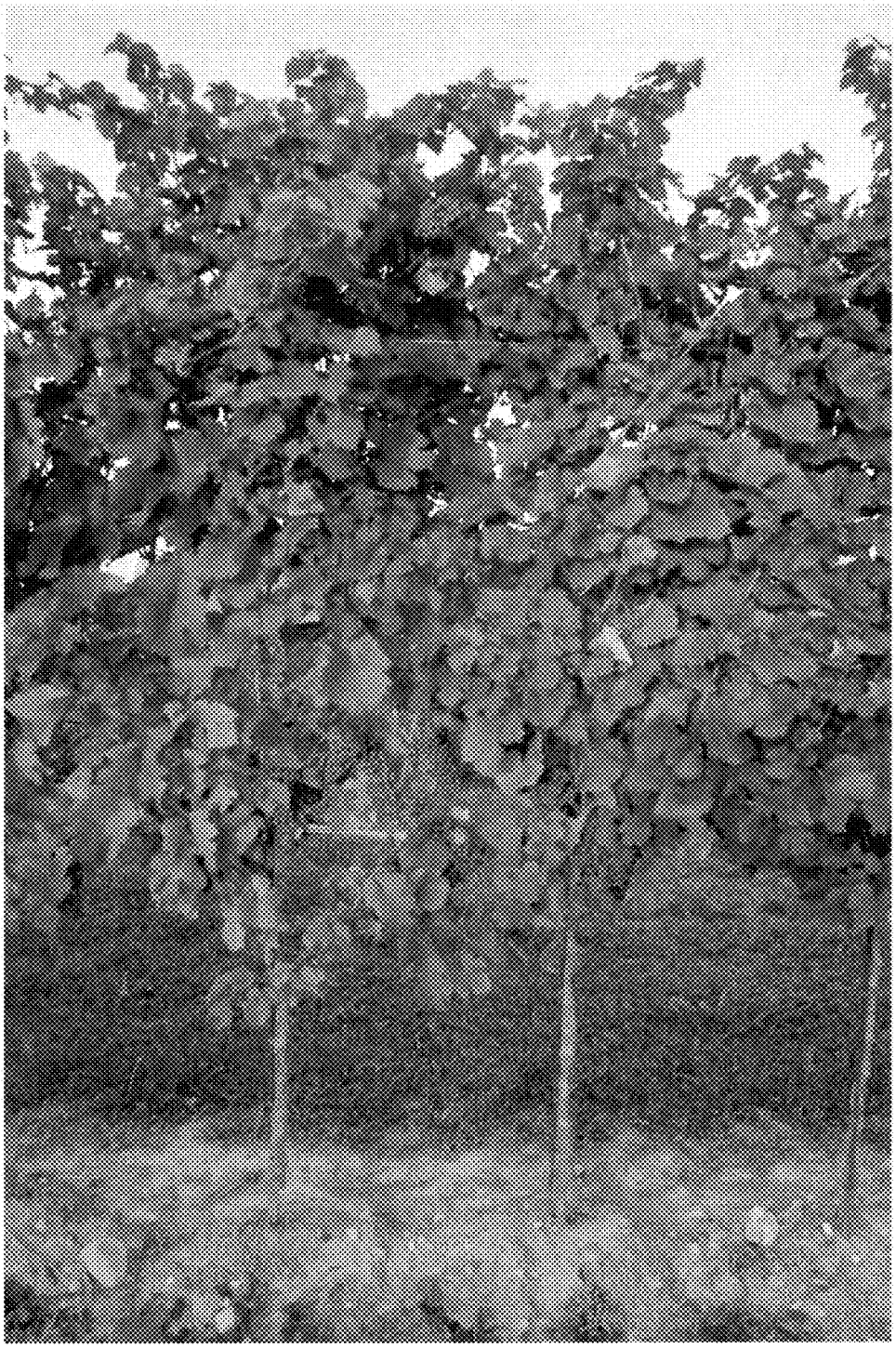
FIG. 4 is a photograph showing four year old plants of the new variety 'TRASEMIS' taken on Sep. 14, 2021, in Rauscedo (PN), Italy.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photographs alone.

DETAILED BOTANICAL DESCRIPTION

The following detailed description of the 'TRASEMIS' variety is based on observations of asexually reproduced progeny. The observed progeny are plants that were 2-4 years of age. The following detailed description concerns plants growing in an open field in Rauscedo (PN), Italy in 2019-2021. The original plant and progeny have been observed growing in a cultivated area in Rauscedo (PN), Italy, with medium texture soil that is rich in skeleton and alluvial in nature. Temperatures in Rauscedo (PN), Italy range from a high of 29° C. to a low of −2° C. Average rainfall is 822 mm per year, with an average rainfall during the growing season (April-September) of 453 mm.

The chart used in the identification of colors described herein is The R.H.S. Colour Chart, 6$^{th}$ edition, except where general color terms of ordinary significance are used. The color values were determined in August-September, 2021 under natural light conditions in Rauscedo (PN), Italy.

Scientific name: *Vitis vinifera* L.

Parentage:

*Seed parent*.—'SK-00-1/10'.

*Pollen parent*.—'TRAMINER'.

Plant:

*Vigor*.—High.

*Growth habit*.—Erect or Semi-Erect.

*Plant height*.—2.0-2.2 m.

*Plant width*.—0.8-1.0 m.

*Trunk diameter*.—5-6 cm.

*Trunk texture*.—Striate.

*Bark coloration*.—RHS 177C.

*Mature cane* (*woody shoot*).—Diameter: Approximately 9.5 mm. Texture: Smooth to Striate. Color: RHS 199B.

Shoot:

*Openness of the shoot tip*.—Fully open for young shoot.

*Distribution of the anthocyanin coloration of the prostrate hairs of the shoot tip*.—Piping.

*Density of prostate hair on the shoot tip*.—High.

*Attitude* (*before tying*).—Erect to Semi-Erect.

*Color of the dorsal side of internodes*.—RHS 144A.

*Color of the ventral side of internodes*.—RHS 144A.

*Distribution of anthocyanin coloration on the bud scales*.—Absent.

*Tendrils*.—Length: Approximately 10.5 cm. Diameter: Approximately 2.04 mm. Color: RHS 152D. Number of Consecutive Tendrils: 2 or less.

Leaves:

*Size*.—Length: approximately 175 mm. Width: approximately 179 mm.

*Shape*.—Circular.

*Number of lobes*.—Five.

*Arrangement*.—Upper lateral sinuses are slightly overlapped and the shape of the base is U; the petiole sinus is closed or overlapping.

*Teeth*.—Medium (approximately 8 mm in length and approximately 8 mm in width).

*Blistering*.—Absent or very weak.

*Density of prostrate hairs*.—Medium to dense (between main veins on lower side of blade).

*Leaf color*.—Immature Leaf: Upper Surface: Green (RHS 152A), some with anthocyanin spots (RHS 167C). Lower Surface: RHS 148A. Mature Leaf: Upper Surface: RHS 143A. Lower Surface: RHS 139C.

*Leaf texture*.—Upper Surface: Smooth. Lower Surface: Very weak goffering.

*Color of veins*.—Upper Surface: RHS 141B. Lower Surface: RHS 141C.

*Petiole*.—Color: RHS 144C with stripes of RHS 184C. Length: 80 mm. Diameter: 4 mm. Texture: Smooth.

*Stem*.—Color: RHS 144A (young); 199B (woody shoot). Length: 1.3-1.5 m. Diameter: 10 mm. Length of Internodes: 9 cm. Texture: Smooth.

*Density of prostrate hairs on petiole*.—None or very low.

*Density of erect hairs on petiole*.—None or very low.

*Depth of upper lateral sinuses*.—44-48 mm.

Flowers:

*Size*.—Length: 3.2 mm. Diameter: 4.4 mm.

*Shape*.—Trapezoidal.

*Bud*.—Shape: Eye. Size: 2.89 mm×2.89 mm. Color: RHS 144A. Typical Time of Bud Burst: April 8$^{th}$ in Rauscedo (PN), Italy.

*Petals*.—Petals per Flower: 5. Shape: Elongated oval. Color: RHS 144A. Petals are fused into a calyptra. Petal Texture: Upper surface is smooth to striate and under surface is smooth. Size: 3.17 mm long; 1.94 mm wide.

*Stamen*.—Fully developed; 5 in number; 3-3.2 mm in length.

*Anthers*.—RHS 9D in color; 1.2-1.5 mm in length.

*Pollen*.—RHS 9D in color.

*Gynoecium*.—Fully developed.

*Pistil*.—Color: RHS 144A. Stigma Length: 0.7-1 mm. Stigma Shape: The top is open. Number of Styles: 1.

*Pedicel*.—Length: 1.5-4 mm. Diameter: 0.5-0.8 mm. Color: RHS 144C.

*Sepals*.—Length: 0.3-0.5 mm. Width (at base): 0.6-0.7 mm. Shape: Triangle. Color: RHS NN137A.

*Quantity of inflorescences*.—11.1 per plant.

*Flowers per flowering stem*.—180.

*Date of bloom*.—Beginning of June in Rauscedo (PN), Italy.

*Lastingness of individual blooms*.—3 days.

*Corolla tube color*.—RHS 144A.

*Corolla tube length*.—3-3.2 mm.

*Corolla texture*.—Smooth.

*Calyx*.—Color: Upper surface is RHS NN137A and lower surface RHS NN137D. Length: 0.3 mm. Width: 1.5 mm. Shape: Pentagon with beveled corners. Margin: Smooth. Texture: Upper surface and lower surface are smooth.

*Fragrance*.—Sweet fragrance with a delicate note of elder and rose.

Fruit:

*Time of beginning of berry ripening*.—August 10 in Rauscedo (PN), Italy.

*Berry shape*.—Globose.

*Berry size*.—Approximately 13 mm in length; and approximately 13 mm in diameter.

*Pruinosity*.—Medium-high.

*Pulp firmness*.—Soft.

*Flesh color*.—RHS 150C.

*Anthocyanin coloration of flesh*.—Absent or very weak; when present, RHS 145C with some RHS 180D.

*Skin*.—Thickness: Thin. Color (without bloom): Yellow rose (RHS 186A).

*Seed*.—Seed Formation: Complete. Number of Seeds: 3-4. Size: 3 mm in length and 1.5-2 mm in width. Color: a mix of RHS 200C and 200D.

*Berry flavor*.—Other than muscat, foxy or herbaceous.

*Harvest time*.—September 4 in Rauscedo (PN), Italy.

*Bunch length* (*peduncle excluded*).—16 cm.

*Bunch width*.—12.5 cm.

*Bunch density*.—Medium.

*Length of peduncle of primary bunch*.—Approximately 50 mm.

*Diameter of peduncle of primary bunch*.—Approximately 4 mm.

*Lignificaiton of peduncle*.—More than the middle.

*Berry hilium*.—Visible.

Use: Wine grape.

Disease/pest resistance: Resistant to downy and powdery mildew.

Must characteristics:

*Total soluble solids* (° *Brix*).—21.9.

*pH*.—3.2.

*Total acidity*.—7.7 g/l.

*Tartaric acid*.—6.9 g/l.

*Malic acid*.—2.8 g/l.

Production characteristics:

*Clusters per shoot*.—1.2.

*Grape production*.—2289 g/plant.

*No. of bunches/vine* (*at harvest*).—11.1.

*Average weight of the bunch*.—202 g.

*Average berry weight*.—1.3 g.

*Pruning wood weight*.—616 g/plant.

*Index of ravaz*.—3.7.

Wine produced from grapes:

*Total acidity*.—7.0 g/l.

*Tartaric acid*.—3.4 g/l.

*pH*.—3.2.

*Net extract*.—20.9 g/l.

*Alcohol*.—12.7 g/l.

*Volatile acidity*.—0.3 g/l.

*Reducing sugars*.—3.8 g/l.

TABLE 3

| Molecular Analysis | | | | | | | | | |
|---|---|---|---|---|---|---|---|---|---|
| VV S2 | | VV MD5 | | VV MD7 | | VV MD25 | | VV MD27 | |
| N + 28 | N 28 | N + 6 | N + 10 | N + 12 | N + 22 | N + 14 | N + 14 | N + 6 | N + 14 |
| | | VV MD28 | | VV MD32 | | VR ZAG 62 | | VR ZAG 79 | |
| | | N + 12 | N + 18 | N + 5 | N + 37 | N + 14 | N + 26 | N + 6 | N + 14 |

Table 3 uses international coding based on "N" (see, European project GENRES 081-A basis for the preservation and utilization of *Vitis* genetic resources).

Phenological characteristics (in Rauscedo (PN), Italy):

*Flowering*.—June 6.

*Veraison* (*change of color*).—August 10.

*Maturation*.—September 4.

We claim:

1. A new and distinct variety of *Vitis vinifera* L. plant substantially as illustrated and described herein.

* * * * *